under the bar code: US011776859B2

(12) United States Patent
Pandey et al.

(10) Patent No.: US 11,776,859 B2
(45) Date of Patent: Oct. 3, 2023

(54) CARE AREA BASED SWATH SPEED FOR THROUGHPUT AND SENSITIVITY IMPROVEMENT (71) Applicant: KLA CORPORATION, Milpitas, CA (US)

(72) Inventors: Anuj Pandey, Delhi (IN); Dong Chen, Singapore (SG); Kwok-Chuen Tan, Singapore (SG)

(73) Assignee: KLA CORPORATION, Milpitas, CA (US)

( * ) Notice: Subject to any disclaimer, the term of this patent is extended or adjusted under 35 U.S.C. 154(b) by 261 days.

(21) Appl. No.: 16/670,158

(22) Filed: Oct. 31, 2019

(65) Prior Publication Data
US 2020/0203237 A1 Jun. 25, 2020

Related U.S. Application Data (60) Provisional application No. 62/801,188, filed on Feb. 5, 2019.

(30) Foreign Application Priority Data

Dec. 19, 2018 (IN) .............................. 201841048098

(51) Int. Cl.
G01N 23/00 (2006.01)
H01L 21/66 (2006.01)
(Continued)

(52) U.S. Cl.
CPC ............. *H01L 22/34* (2013.01); *G01N 23/20* (2013.01); *G06T 7/001* (2013.01); *G06T 7/0006* (2013.01);
(Continued)

(58) Field of Classification Search
CPC .. H01L 22/00–20; G01N 23/20; G01N 23/00; G06T 2207/30148; H01J 37/28;
(Continued)

(56) References Cited

U.S. PATENT DOCUMENTS 6,054,713 A 4/2000 Miyake et al.
6,633,363 B1 10/2003 Makinouchi
(Continued)

FOREIGN PATENT DOCUMENTS

EP 2599114 B1 1/2018
KR 20180001564 A 1/2018
WO 2018183096 A1 10/2018

OTHER PUBLICATIONS

WIPO, ISR for PCT/US2019/066434, Apr. 17, 2020.

*Primary Examiner* — Joseph P Martinez
(74) *Attorney, Agent, or Firm* — HODGSON RUSS LLP (57) ABSTRACT Embodiments may include methods, systems, and apparatuses for care area based swath speed for throughput and sensitivity improvement. A method may comprise receiving scan region of a die. The scan region of the die may have a first care area at a controller configured to control an inspection tool, wherein the inspection tool includes a stage having the die disposed thereon. The method may then include scanning a first portion of the scan region at a fast feed rate and the first care area at a slow feed rate. Scanning may include emitting particles in a particle beam toward the die resulting an incidence on the die. Emitting may be performed using a particle emitter. Scanning may then include detecting a portion of particles reflected from the incidence. Detecting may be performed using a detector. Scanning may then include changing a position of the stage relative to the incidence.

18 Claims, 5 Drawing Sheets (51) Int. Cl.
*G06T 7/00* (2017.01)
*H01L 21/683* (2006.01)
*G01N 23/20* (2018.01)

(52) U.S. Cl.
CPC .......... *H01L 21/6836* (2013.01); *H01L 22/12* (2013.01); *G01N 23/00* (2013.01); *G06T 2207/30148* (2013.01); *H01L 2221/68331* (2013.01)

(58) Field of Classification Search
CPC ... H01J 2237/20228; H01J 2237/20221; H01J 2237/20278
USPC .......................................................... 250/307
See application file for complete search history.

(56) References Cited

U.S. PATENT DOCUMENTS

| | | | |
|---|---|---|---|
| 7,315,022 B1 | 1/2008 | Adler et al. | |
| 7,335,611 B2 | 2/2008 | Ramaswamy et al. | |
| 7,525,325 B1 | 4/2009 | Jenkins et al. | |
| 8,126,255 B2 | 2/2012 | Bhaskar et al. | |
| 8,817,249 B2 | 8/2014 | Gastaldo et al. | |
| 8,975,582 B2* | 3/2015 | Nishiyama | H01J 37/28 356/237.4 |
| 9,171,364 B2 | 10/2015 | Wu et al. | |
| 9,401,014 B2 | 7/2016 | Zafar et al. | |
| 9,601,314 B2 | 3/2017 | Ninomiya et al. | |
| 9,812,290 B2* | 11/2017 | Phaneuf | H01J 37/222 |
| 9,881,817 B1* | 1/2018 | Lam | H01J 37/3172 |
| 10,347,460 B2* | 7/2019 | Zhao | H01J 37/28 |
| 2010/0072365 A1* | 3/2010 | Shoham | H01J 37/222 250/311 |
| 2011/0163230 A1 | 7/2011 | Hiroi et al. | |
| 2015/0060666 A1* | 3/2015 | Hatakeyama | H01J 37/29 250/307 |
| 2016/0351373 A1 | 12/2016 | Xiao et al. | |
| 2017/0344697 A1* | 11/2017 | Postolov | G06F 30/398 |
| 2018/0190581 A1 | 7/2018 | Lin | |
| 2018/0276808 A1 | 9/2018 | Brauer et al. | |

\* cited by examiner

CARE AREA BASED SWATH SPEED FOR THROUGHPUT AND SENSITIVITY IMPROVEMENT

CROSS REFERENCE TO RELATED APPLICATIONS

This application claims priority to Indian Provisional Patent Application 201841048098, filed Dec. 19, 2018 and U.S. Provisional Application No. 62/801,188, filed on Feb. 5, 2019, the entire disclosures of which are hereby incorporated by reference.

FIELD OF THE DISCLOSURE

The disclosure generally relates to semiconductor metrology. More particularly the disclosure generally relates to inspection of dies.

BACKGROUND OF THE DISCLOSURE

Evolution of the semiconductor manufacturing industry is placing greater demands on yield management and, in particular, on metrology and inspection systems. Critical dimensions continue to shrink, yet the industry needs to decrease time for achieving high-yield, high-value production. Minimizing the total time from detecting a yield problem to fixing it determines the return-on-investment for a semiconductor manufacturer.

In advanced wafer-level packaging (aWLP), there is a desire to fabricate thin line-space (L/S) redistribution layers (RDLs) to improve device performance. RDLs with dimensions as small as 2 μm have already entered production, and packages with even smaller RDLs may be expected in the future.

RDLs, including those fine-pitch RDLs discussed herein, serve to connect two or more dies needing to be packaged together. RDL inspection is often an important part of semiconductor manufacturing, and is highly correlated to yield.

Current inspection tool stage architecture only provides for constant-speed (or constant-feed rate) scanning. That is, the stage speed is constant (e.g., it may be one-quarter of full speed, one-half of full speed, or full speed) during the entire scan. If the scan speed, also referred to herein as the feed rate, is made slow to increase sensitivity, the entire die—including portions not relevant to the inspection—must be scanned at a slow feed rate. If the feed rate is increased to improve throughput, sensitivity of the inspection decreases. This brings about inefficiencies and inaccuracies in the wafer inspection process.

Therefore, improved methods of inspecting RDLs or other devices on a semiconductor wafer are necessary.

SUMMARY OF THE DISCLOSURE

Embodiments may include methods, systems, and apparatuses for care area based swath speed for throughput and sensitivity improvement.

An embodiment may be a method comprising receiving scan region of a die. The scan region of the die may have a first care area at a controller configured to control an inspection tool, wherein the inspection tool includes a stage having the die disposed thereon. The method may then include scanning a first portion of the scan region at a fast feed rate and the first care area at a slow feed rate. The scanning may be performed using the inspection tool. The scanning may include emitting particles in a particle beam toward the die resulting an incidence on the die. The emitting may be performed using a particle emitter. The scanning may then include detecting a portion of particles reflected from the incidence. The detecting may be performed using a detector. The scanning may then include changing a position of the stage relative to the incidence.

An embodiment may be a system comprising an inspection tool and a controller. The inspection tool may include a particle emitter, a stage, and a detector. The particle emitter may be configured to emit particles in a particle beam. The stage may be configured to hold a die in a path of the particle beam emitted by the particle emitter. The detector may be configured to detect a portion of the particles reflected by the die.

The controller may be in electronic communication with the inspection tool. The controller may be configured to receive a scan region of the die. The scan region of the die may have a first care area. The controller may be further configured to instruct the inspection tool to scan a first portion of the scan region at a fast feed rate.

The scan may include emitting, using the particle emitter, particles in a particle beam toward the die, which may result in an incidence on the die. The scan may further include detecting, using the detector, the portion of particles reflected from the incidence. The scan may further include changing a position of the stage relative to the incidence.

An embodiment may be a non-transitory, computer-readable storage medium comprising one or more programs. The one or more programs may be for executing steps on one or more computing devices. The steps may include instructing an inspection tool to receive a scan region of a die having a first care area at a controller configured to control the inspection tool and sending instructions to the inspection tool to change a position of the stage relative to an incidence, thereby scanning a first portion of the scan region at a fast feed rate and the first care area at a slow feed rate. The inspection tool may include a stage having the die disposed thereon.

In various embodiments, the first portion of the scan region may be not within the first care area.

In various embodiments, the slow feed rate may be less than the fast feed rate.

In various embodiments, the scan region may have a second care area. The method or instructing the inspection tool may further comprise scanning, using the inspection tool, a second portion of the scan region at the fast feed rate, and the second care area at the slow feed rate.

In various embodiments, the second portion of the scan region may be not within the first care area nor within the second care area.

In various embodiments, changing the position of the stage relative to the incidence may comprise moving one or more of the stage, the detector, the emitter, or the particle beam.

In various embodiments, the magnitude of the fast feed rate may be two to four times the magnitude of the slow feed rate.

In various embodiments, the first care area may comprise a polygonal boundary.

In various embodiments, the particle emitter may comprise a light emitter. The detector may comprise a light detector.

In various embodiments, the detector may be a time delay and integration image sensor.

In various embodiments, the first care area may comprise a redistribution layer region. The first portion of the scan region may be not the redistribution layer region.

BRIEF DESCRIPTION OF THE FIGURES

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Throughput may represent a quantity of specimens (e.g., dies, wafers) processed in a given time. It is desirable to maximize throughput, in order to reduce inspection time and therefore total production time. Further, increased throughput may also reduce costs associated with semiconductor inspection and production.

Sensitivity, which is the ability to detect tiny defects, may be desirable in semiconductor manufacturing processes.

Wafer Level Packaging segment is an umbrella term used for all the packaging process in which die packages are made prior to dies being diced, i.e., at the wafer-level itself. Advanced Wafer Level Packaging refers to latest state-of-the-art techniques for developing such wafer level packages which including fabricating small design rule line-space/via patterns. Embodiments disclosed herein include methods and systems exhibiting improved throughput and sensitivity for semiconductor inspection (e.g., RDL inspection). Such embodiments may improve inspection throughput while scanning the wafer by implementing a variable feed rate scan.

A die may be inspected using a particle emitter and a detector configured to scan the die at an incidence. The incidence may be the location (e.g., point, line, or area) where the beam from the emitter falls incident on the die and reflects, where a portion of the reflected beam is captured by the detector. It should be noted that the incidence may be a point, a line, or an area on the die.

The feed rate of the scan may be the speed at which a die and an incidence on the die move relative to each other, regardless of which component (e.g., the stage, detector, emitter, or particle beam) is actually moving. A particle beam may be a light beam, electron beam, or ion beam. Since high sensitivity when inspecting RDLs is desirable, implementing a slow feed rate scan of each RDL is advantageous, as it improves signal from a detector such as a time delay and integration (TDI) sensor. Thus, embodiments of the present disclosure may implement a slow feed rate while scanning an RDL and a fast feed rate while scanning an area outside of the RDL. This is accomplished using, inter alia, a care area.

In some embodiments, the stage is preferably moving. Such movement of the stage may be accomplished by means for moving the stage. Such means for moving the stage may include, for example, one or more servo motors, stepper motor(s), or other means for moving the stage.

By implementing variable feed rate scanning, embodiments of the present disclosure may increase sensitivity while maintaining high throughput. This is because less time is spent on the regions outside of the regions of interest of the inspection (i.e., outside the RDLs).

Figure 1:
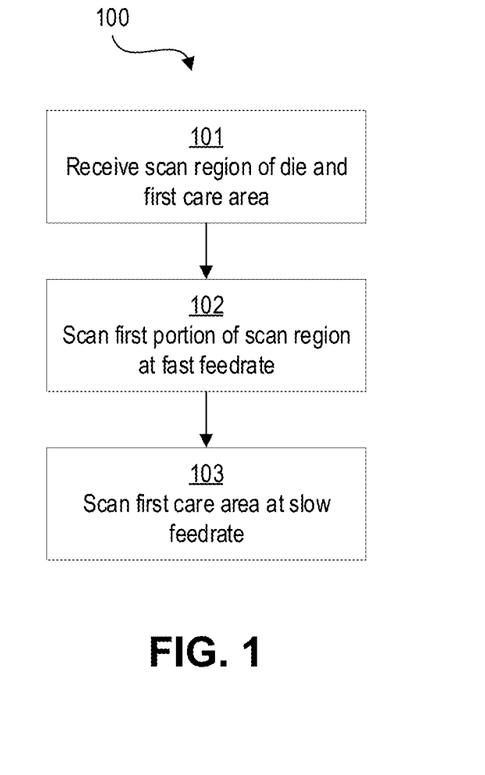
FIG. 1 illustrates a method for performing a scan in accordance with an embodiment of the present disclosure.

An embodiment is a method, such as method 100 illustrated in FIG. 1. Method 100 may include, at 101, receiving a scan region of a die and a first care area contained therein at a controller. The controller may be configured to control an inspection tool. The inspection tool may include a stage. The stage may have a die disposed thereon.

Next, the method may include scanning, using the inspection tool, a first portion of the scan region at 102 and the first care area at 103. At 102, the first portion of the scan region may be scanned at a fast feed rate. The first portion of the scan region may be outside of the first care area, e.g., not within the first care area. At 103, the first care area may be scanned at a slow feed rate.

It should be noted that in another embodiment, steps 102 and 103 may be in reverse order if the scan begins within a first care area.

Figure 2:
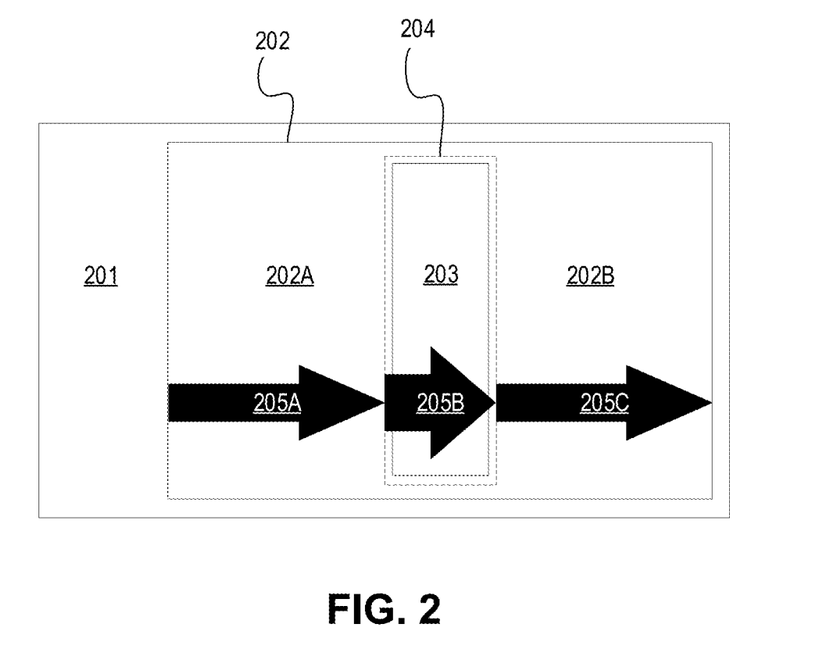
FIG. 2 illustrates an example scan in accordance with an embodiment of the present disclosure.

FIG. 2 illustrates an example implementation of method 100 used to inspect scan region 202 on die 201. A scan (205A, 205B, 205C) of scan region 202 may begin with an incidence scanning (205A) first portion 202A of scan region 202. While scanning across the first portion of the scan region (205A), the scan feed rate may be a fast feed rate. As soon as the incidence crosses into first care area 204, which substantially approximates RDL region 203, the scan feed rate may change to a slow feed rate. At the slow feed rate, first care area 204 may be scanned (205B). As the incidence crosses out of first care area 204, for example, into second portion 202B of scan region 202, the feed rate may return to a fast feed rate, and continue scanning (205C) until reaching the end of scan region 202. It should be noted that the scan may finish at first care area 204.

Figure 3:
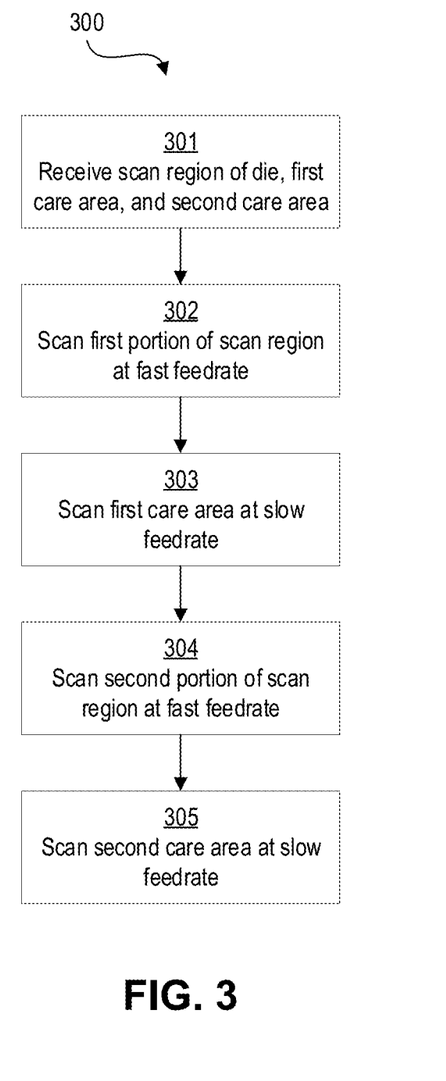
FIG. 3 illustrates a method for performing a scan in accordance with an embodiment of the present disclosure.

In another embodiment, method 300 may be employed with two care areas, as illustrated in FIG. 3. At 301, the controller may receive a scan region containing a first care area and a second care area. Method 300 may include scanning, using the inspection tool, a first portion of the scan region at 302 and the first care area at 303. At 302, the first portion of the scan region may be scanned at a fast feed rate. The first portion of the scan region may be outside of the first care area and the second care area, e.g., not within the first care area nor the second care area. At 303, the first care area may be scanned at a slow feed rate. Method 300 may then include scanning, using the inspection tool, a second portion of the scan region at 304 and the second care area at 305. At 304, the second portion of the scan region may be scanned at the fast reed rate. The second portion of the scan region may be outside of the first care area and the second care area, e.g., not within the first care area nor the second care area. The second portion of the scan region may be the region between the first care area and the second care area. At 305, the second care area may then be scanned at a slow feed rate.

It should be noted that in another embodiment, steps 302, 303, 304, and 305 may be in a different order depending on where the scan begins (whether it begins in the first or second care area or the first or second portion of the scan region).

Figure 4:
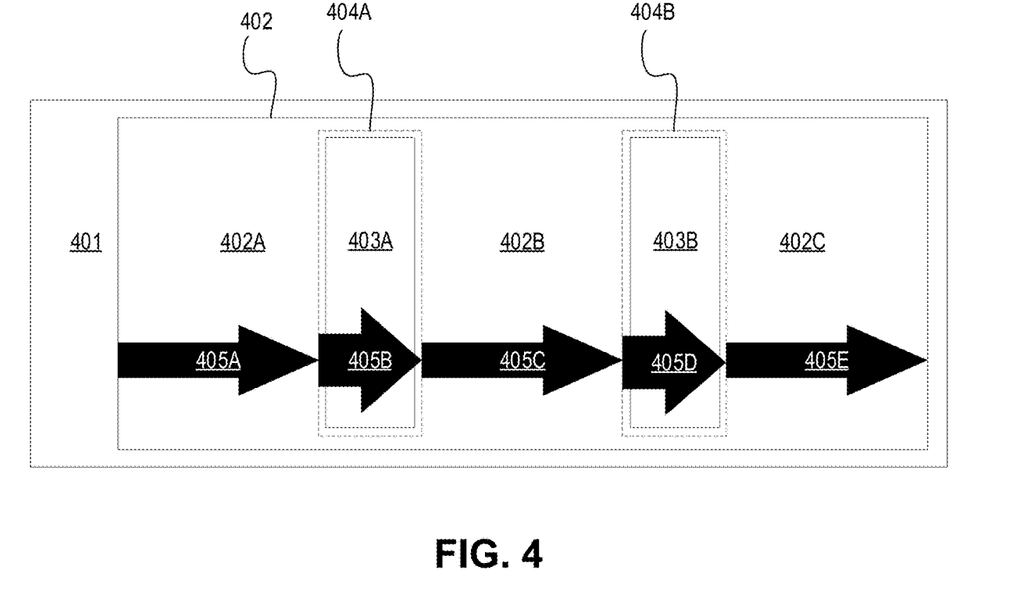
FIG. 4 illustrates an example scan in accordance with an embodiment of the present disclosure.

FIG. 4 illustrates an example implementation of method 300 used to inspect scan region 402 on die 401. A scan (405A, 405B, 405C, 405D, and 405E) of scan region 402 may begin with an incidence scanning (405A) first portion 402A of scan region 402. While scanning across the first portion of the scan region (405A), the scan feed rate may be a fast feed rate. As soon as the incidence crosses into first care area 404A, which substantially approximates RDL region 403A, the scan feed rate may change to a slow feed rate. At the slow feed rate, first care area 404A may be scanned (405B). As the incidence crosses out of first care area 404A, for example, into second portion 402B of the scan region, the feed rate may return to the fast feed rate, and continue scanning (405C) until reaching second care area 404B. As the incidence then crosses into second care area 404B, which substantially approximates RDL region 403B, the scan feed rate may change to the slow feed rate. At the slow feed rate, second care area 404B may be scanned (405D). As the incidence crosses out of second care area 404B, for example, into a third portion 402C of the scan region, the feed rate may return to the fast feed rate, and continue scanning (405E) until reaching the end of scan region 402. It should be noted that the scan may finish at second care area 404B.

According to the present disclosure, there may be one or more care areas in a scan region of a die. An incidence may traverse the scan region, scanning at a fast feed rate within those portions of the die not within a care area, and at a slow feed rate within the care areas. Care areas may be placed in such a way that a care area necessitating a slow feed rate scan is sandwiched between care areas permitting a fast feed rate scan.

Given a completed wafer alignment, stage movement may be guided by system coordinates, thus moving the stage relative to the optics precisely. In this way, the system may be able to determine, based on coordinates which, if any, care area contains the location being scanned at any given time.

Figure 5:
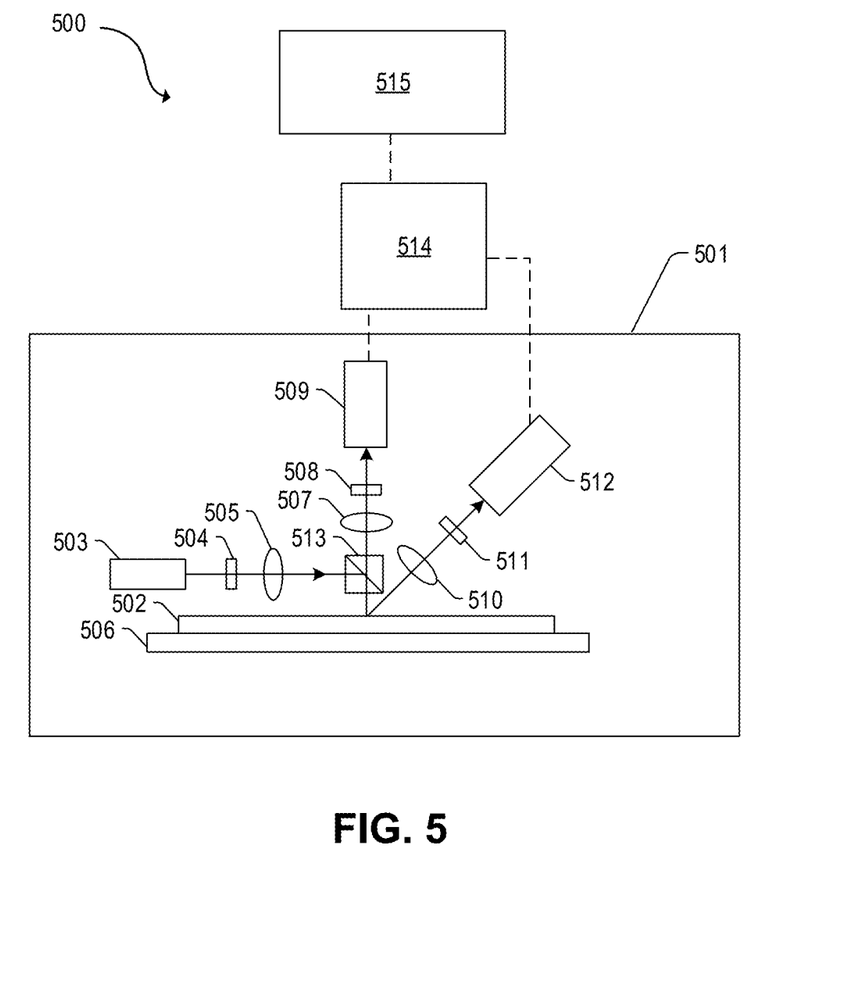
FIG. 5 illustrates an example system configured to perform a scan in accordance with an embodiment of the present disclosure.

With reference to FIG. 5, the scanning in methods 100 or 300 may include emitting, using a particle emitter such as particle emitter 503, particles in a particle beam. The emission of the particle beam may be toward the die, such as specimen 502 disposed on stage 506, resulting in an incidence of the beam on the die. A detector, such as detector 509 or detector 512 may be used to detect a portion of particles reflected from the incidence. While detecting, the position of the stage relative to the incidence may be changed. The detection during the changing of the position may be incremental or continuous, e.g., incremental or continuous scanning.

In incremental scanning, an emission from the emitter and/or a detection by the detector may occur at predefined or calculated intervals. The intervals may be distance intervals, angle intervals, time intervals, or some combination of the same.

In continuous scanning, the emitter may continuously emit the particle beam, and the detector may be detecting continuously (e.g., at a fine increment).

Changing the position of the stage relative to the incidence may include moving one or more of the stage, the detector, the emitter, or the particle beam. Moving the stage, detector, or emitter may be accomplished by appropriate means, such as, inter alia, servo motors or other actuators. Moving the particle beam may be accomplished by appropriate means, such as, inter alia, refractive lenses, mirrors, or other optical means.

The fast feed rate may be comparatively faster than the slow feed rate, e.g., the magnitude of the fast feed rate may be greater than the magnitude of the slow feed rate. The difference between the fast feed rate and the slow feed rate, and/or magnitudes thereof, may be determined based on, for example, the wafer material, defect types, inspection layer (photo, seed, etch etc.), defect type, or other process parameters. In some embodiments, the magnitude of the fast feed rate may be four times the magnitude of the slow feed rate. In some other embodiments, the magnitude of the fast feed rate may be twice the magnitude of the slow feed rate. In other embodiments, the magnitude of the fast feed rate may be two to four times the magnitude of the slow feed rate. Such a range may set out a lower limit value and an upper limit value, and include all values to the magnitude of the smallest value (either lower limit value or upper limit value) and ranges between the values of the stated range.

A care area may be an area of the wafer (or die on the wafer or a scan region) that is desired to be inspected by the inspection tool. The care area is usually smaller than the field-of-view, or scan region. A field-of-view, or scan region, may include one or more care areas. A care area, such as the first care area or the second care are, may comprise a polygonal boundary. Such a care area may be pre-determined based on a design, or may be calculated on a per-die basis. The care area, such as the first care area or the second care area, may comprise a RDL region. In such embodiments, the first and/or second portions of the scan region is not the RDL region.

The detector may be a TDI sensor. A TDI sensor may be a charge coupled device configured to optimally capture images of moving objects. A TDI sensor comprises an array of pixels, or an array of lines of pixels, to capture images of an object as the object moves relative to the sensor. Each pixel or line of pixels shift their partial measurements to the adjacent pixel or line of pixels synchronously with the motion of the image across the array. In this way, a TDI sensor may image the reflection of a moving incidence on an object from a light beam. Thus, a TDI sensor is able to attain high sensitivity when imaging moving objects.

In an embodiment, the particle emitter may comprise a light emitter and the detector may comprise a light detector.

Another embodiment may be a system comprising an inspection tool and a controller. The inspection tool may include a particle emitter, a stage, and a detector. The particle emitter may be configured to emit particles in a particle beam. The stage may be configured to hold a die in a path of the particle beam emitted by the particle emitter. The detector may be configured to detect a portion of the particles reflected by the die (e.g., the specimen on the stage).

The controller may be in electronic communication with the inspection tool the controller may be external to the inspection tool or internal (e.g., on-board) to the inspection tool. The controller may be configured to implement, using the tool, a method such as method 100 or method 300.

One embodiment of a system 500 is shown in FIG. 5. The system 500 includes optical based subsystem 501. In general, the optical based subsystem 501 is configured for generating optical based output for a specimen 502 by directing light to (or scanning light over) and detecting light from the specimen 502. In one embodiment, the specimen 502 includes a wafer. The wafer may include any wafer known in the art. In another embodiment, the specimen includes a reticle. The reticle may include any reticle known in the art.

In the embodiment of the system 500 shown in FIG. 5, optical based subsystem 501 includes an illumination subsystem configured to direct light to specimen 502. The illumination subsystem includes at least one light source. For example, as shown in FIG. 5, the illumination subsystem includes light source 503. In one embodiment, the illumination subsystem is configured to direct the light to the specimen 502 at one or more angles of incidence, which may include one or more oblique angles and/or one or more normal angles. For example, as shown in FIG. 5, light from light source 503 is directed through optical element 504 and then lens 505 to specimen 502 at an oblique angle of incidence. The oblique angle of incidence may include any suitable oblique angle of incidence, which may vary depending on, for instance, characteristics of the specimen 502.

The optical based subsystem 501 may be configured to direct the light to the specimen 502 at different angles of incidence at different times. For example, the optical based subsystem 501 may be configured to alter one or more characteristics of one or more elements of the illumination subsystem such that the light can be directed to the specimen 502 at an angle of incidence that is different than that shown in FIG. 5. In one such example, the optical based subsystem 501 may be configured to move light source 503, optical element 504, and lens 505 such that the light is directed to the specimen 502 at a different oblique angle of incidence or a normal (or near normal) angle of incidence.

In some instances, the optical based subsystem 501 may be configured to direct light to the specimen 502 at more than one angle of incidence at the same time. For example, the illumination subsystem may include more than one illumination channel, one of the illumination channels may include light source 503, optical element 504, and lens 505 as shown in FIG. 5 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen 502 at different angles of incidence may be different such that light resulting from illumination of the specimen 502 at the different angles of incidence can be discriminated from each other at the detector(s).

In another instance, the illumination subsystem may include only one light source (e.g., light source 503 shown in FIG. 5) and light from the light source may be separated into different optical paths (e.g., based on wavelength, polarization, etc.) by one or more optical elements (not shown) of the illumination subsystem. Light in each of the different optical paths may then be directed to the specimen 502. Multiple illumination channels may be configured to direct light to the specimen 502 at the same time or at different times (e.g., when different illumination channels are used to sequentially illuminate the specimen). In another instance, the same illumination channel may be configured to direct light to the specimen 502 with different characteristics at different times. For example, in some instances, optical element 504 may be configured as a spectral filter and the properties of the spectral filter can be changed in a variety of different ways (e.g., by swapping out the spectral filter) such that different wavelengths of light can be directed to the specimen 502 at different times. The illumination subsystem may have any other suitable configuration known in the art for directing the light having different or the same characteristics to the specimen 502 at different or the same angles of incidence sequentially or simultaneously.

In one embodiment, light source 503 may include a broadband plasma (BBP) source. In this manner, the light generated by the light source 503 and directed to the specimen 502 may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source 503 may also include a polychromatic light source that generates light at multiple discrete wavelengths or wavebands.

Light from optical element 504 may be focused onto specimen 502 by lens 505. Although lens 505 is shown in FIG. 5 as a single refractive optical element, it is to be understood that, in practice, lens 505 may include a number of refractive and/or reflective optical elements that in combination focus the light from the optical element to the specimen. The illumination subsystem shown in FIG. 5 and described herein may include any other suitable optical elements (not shown). Examples of such optical elements include, but are not limited to, polarizing component(s), spectral filter(s), spatial filter(s), reflective optical element (s), apodizer(s), beam splitter(s) (such as beam splitter 513), aperture(s), and the like, which may include any such suitable optical elements known in the art. In addition, the optical based subsystem 501 may be configured to alter one or more of the elements of the illumination subsystem based on the type of illumination to be used for generating the optical based output.

The optical based subsystem 501 may also include a scanning subsystem configured to cause the light to be scanned over the specimen 502. For example, the optical based subsystem 501 may include stage 506 on which specimen 502 is disposed during optical based output generation. The scanning subsystem may include any suitable mechanical and/or robotic assembly (that includes stage 506) that can be configured to move the specimen 502 such that the light can be scanned over the specimen 502. In addition, or alternatively, the optical based subsystem 501 may be configured such that one or more optical elements of the optical based subsystem 501 perform some scanning of the light over the specimen 502. The light may be scanned over the specimen 502 in any suitable fashion such as in a serpentine-like path or in a spiral path.

The optical based subsystem 501 further includes one or more detection channels. At least one of the one or more detection channels includes a detector configured to detect light from the specimen 502 due to illumination of the specimen 502 by the subsystem and to generate output responsive to the detected light. For example, the optical based subsystem 501 shown in FIG. 5 includes two detection channels, one formed by collector 507, element 508, and detector 509 and another formed by collector 510, element 511, and detector 512. As shown in FIG. 5, the two detection channels are configured to collect and detect light at different angles of collection. In some instances, both detection channels are configured to detect scattered light, and the detection channels are configured to detect tight that is scattered at different angles from the specimen 502. However, one or more of the detection channels may be configured to detect another type of light from the specimen 502 (e.g., reflected light).

As further shown in FIG. 5, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 510, element 511, and detector 512 may be configured to collect and detect light that is scattered out of the plane of incidence. Therefore, such a detection channel may be commonly referred to as a "side" channel, and such a side channel may be centered in a plane that is substantially perpendicular to the plane of incidence.

Although FIG. 5 shows an embodiment of the optical based subsystem 501 that includes two detection channels, the optical based subsystem 501 may include a different number of detection channels (e.g., only one detection channel or two or more detection channels). In one such instance, the detection channel formed by collector 510, element 511, and detector 512 may form one side channel as described above, and the optical based subsystem 501 may include an additional detection channel (not shown) formed as another side channel that is positioned on the opposite side of the plane of incidence. Therefore, the optical based subsystem 501 may include the detection channel that includes collector 507, element 508, and detector 509 and that is centered in the plane of incidence and configured to collect and detect light at scattering angle(s) that are at or close to normal to the specimen 502 surface. This detection channel may therefore be commonly referred to as a "top" channel, and the optical based subsystem 501 may also include two or more side channels configured as described above. As such, the optical based subsystem 501 may include at least three channels (i.e., one top channel and two side channels), and each of the at least three channels has its own collector, each of which is configured to collect light at different scattering angles than each of the other collectors.

As described further above, each of the detection channels included in the optical based subsystem 501 may be configured to detect scattered light. Therefore, the optical based subsystem 501 shown in FIG. 5 may be configured for dark field (DF) output generation for specimens 502. However, the optical based subsystem 501 may also or alternatively include detection channel(s) that are configured for bright field (BF) output generation for specimens 502. In other words, the optical based subsystem 501 may include at least one detection channel that is configured to detect light specularly reflected from the specimen 502. Therefore, the optical based subsystems 501 described herein may be configured for only DF, only BF, or both DF and BF imaging. Although each of the collectors are shown in FIG. 5 as single refractive optical elements, it is to be understood that each of the collectors may include one or more refractive optical die(s) and/or one or more reflective optical element(s).

The one or more detection channels may include any suitable detectors known in the art. For example, the detectors may include photo-multiplier tubes (PMTs), charge coupled devices (CCDs), TDI cameras, and any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the optical based subsystem may be signals or data, but not image signals or image data. In such instances, a processor such as processor 514 may be configured to generate images of the specimen 502 from the non-imaging output of the detectors. However, in other instances, the detectors may be configured as imaging detectors that are configured to generate imaging signals or image data. Therefore, the optical based subsystem may be configured to generate optical images or other optical based output described herein in a number of ways.

It is noted that FIG. 5 is provided herein to generally illustrate a configuration of an optical based subsystem 501 that may be included in the system embodiments described herein or that may generate optical based output that is used by the system embodiments described herein. The optical based subsystem 501 configuration described herein may be altered to optimize the performance of the optical based subsystem 501 as is normally performed when designing a commercial output acquisition system. In addition, the systems described herein may be implemented using an existing system (e.g., by adding functionality described herein to an existing system). For some such systems, the methods described herein may be provided as optional functionality of the system (e.g., in addition to other functionality of the system). Alternatively, the system described herein may be designed as a completely new system.

The processor 514 may be coupled to the components of the system 500 in any suitable manner (e.g., via one or more transmission media, which may include wired and/or wireless transmission media) such that the processor 514 can receive output. The processor 514 may be configured to perform a number of functions using the output. The system 500 can receive instructions or other information from the processor 514. The processor 514 and/or the electronic data storage unit 515 optionally may be in electronic communication with a wafer inspection tool, a wafer metrology tool, or a wafer review tool (not illustrated) to receive additional information or send instructions. For example, the processor 514 and/or the electronic data storage unit 515 can be in electronic communication with an SEM.

The processor 514, other system(s), or other subsystem(s) described herein may be part of various systems, including a personal computer system, image computer, mainframe computer system, workstation, network appliance, internet appliance, or other device. The subsystem(s) or system(s) may also include any suitable processor known in the art, such as a parallel processor. In addition, the subsystem(s) or system(s) may include a platform with high-speed processing and software, either as a standalone or a networked tool.

The processor 514 and electronic data storage unit 515 may be disposed in or otherwise part of the system 500 or another device. In an example, the processor 514 and electronic data storage unit 515 may be part of a standalone control unit or in a centralized quality control unit. Multiple processors 514 or electronic data storage units 515 may be used.

The processor 514 may be implemented in practice by any combination of hardware, software, and firmware. Also, its functions as described herein may be performed by one unit, or divided up among different components, each of which may be implemented in turn by any combination of hardware, software and firmware. Program code or instructions for the processor 514 to implement various methods and functions may be stored in readable storage media, such as a memory in the electronic data storage unit 515 or other memory.

If the system 500 includes more than one processor 514, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

The processor 514 may be configured to perform a number of functions using the output of the system 500 or other output. For instance, the processor 514 may be configured to send the output to an electronic data storage unit 515 or another storage medium. The processor 514 may be further configured as described herein.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

The processor 514 may be configured according to any of the embodiments described herein. The processor 514 also may be configured to perform other functions or additional steps using the output of the system 500 or using images or data from other sources.

Various steps, functions, and/or operations of system 500 and the methods disclosed herein are carried out by one or more of the following: electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape, and the like. A carrier medium may include a transmission medium such as a wire, cable, or wireless transmission link. For instance, the various steps described throughout the present disclosure may be carried out by a single processor 514 or, alternatively, multiple processors 514. Moreover, different subsystems of the system 500 may include one or more computing or logic systems. Therefore, the above description should not be interpreted as a limitation on the present disclosure but merely an illustration.

In an instance, the processor 514 is in communication with the system 500. The processor 514 may be configured to receive a scan region of the die and a first care area contained therein. The processor 514 may be further configured to instruct the system 501 to scan a first portion of the scan region at a fast feed rate and the first care area at a slow feed rate. The first portion of the scan region may be outside of the first care area.

The scan region received may further include a second care area. The processor 514 may be further configured to instruct the inspection tool to scan a second portion of the scan region at a fast feed rate and the second care area at a slow feed rate. The second portion of the scan region may be outside of the first care area and the second care area, e.g., between the first and second care areas.

The scan may include emitting, using emitter 503, the particles in a particle beam toward the die (specimen 502) resulting in an incidence on the die; detecting, using detector 509 or 512, the portion of particles reflected from the incidence; and changing a position of stage 506 relative to the incidence.

An additional embodiment relates to a non-transitory computer-readable medium storing program instructions executable on a controller for performing a computer-implemented method for determining a height of an illuminated region on a surface of a specimen 502, as disclosed herein. In particular, as shown in FIG. 5, electronic data storage unit 515 or other storage medium may contain non-transitory computer-readable medium that includes program instructions executable on the processor 514. The computer-implemented method may include any step(s) of any method(s) described herein, including methods 100 or 300.

Program instructions implementing methods such as those described herein may be stored on computer-readable medium, such as in the electronic data storage unit 515 or other storage medium. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), Streaming SIMD Extension (SSE), or other technologies or methodologies, as desired.

The steps of the method described in the various embodiments and examples disclosed herein are sufficient to carry out the methods of the present invention. Thus, in an embodiment, the method consists essentially of a combination of the steps of the methods disclosed herein. In another embodiment, the method consists of such steps.

Although the present disclosure has been described with respect to one or more particular embodiments, it will be understood that other embodiments of the present disclosure may be made without departing from the scope of the present disclosure.

What is claimed is:

1. A method, comprising:
   receiving a scan region of a die having a first care area at a controller configured to control an optical inspection tool, wherein the optical inspection tool includes a stage having the die disposed thereon; and
   optically scanning, using the optical inspection tool:
   a first portion of the scan region within the die at a fast feed rate, wherein the first portion of the scan region is not within the first care area; and
   the first care area within the die at a slow feed rate, wherein the slow feed rate is less than the fast feed rate;
   wherein the optical scanning includes:
   emitting, using a light emitter, a light beam toward the die resulting in an incidence on the die;
   detecting, using a light detector, a portion of the light beam reflected from the incidence; and
   changing a position of the stage relative to the incidence.

2. The method of claim 1, wherein the scan region has a second care area, and wherein the method further comprises optically scanning, using the optical inspection tool:

a second portion of the scan region within the die at the fast feed rate, wherein the second portion of the scan region is not within the first care area nor within the second care area; and the second care area within the die at the slow feed rate.

3. The method of claim 1, wherein changing the position of the stage relative to the incidence comprises moving one or more of the stage, the light detector, the light emitter, or the light beam.

4. The method of claim 1, wherein the magnitude of the fast feed rate is two to four times the magnitude of the slow feed rate.

5. The method of claim 1, wherein the first care area comprises a polygonal boundary.

6. The method of claim 1, wherein the light detector is a time delay and integration image sensor.

7. The method of claim 1, wherein the first care area comprises a redistribution layer region and the first portion of the scan region is not the redistribution layer region.

8. A system, comprising:
an optical inspection tool including:
a light emitter configured to emit particles in a light beam;
a stage configured to hold a die in a path of the light beam emitted by the light emitter;
a light detector configured to detect a portion of the light beam reflected by the die; and
a controller in electronic communication with the optical inspection tool; and
wherein the controller is configured to:
receive a scan region of the die having a first care area; and
instruct the optical inspection tool to optically scan:
a first portion of the scan region within the die at a fast feed rate, wherein the first portion of the scan region is not within the first care area; and
the first care area within the die at a slow feed rate, wherein the slow feed rate is less than the fast feed rate;
wherein the optical scan includes:
emitting, using the light emitter, the light beam toward the die resulting in an incidence on the die;
detecting, using the light detector, the portion of light beam reflected from the incidence; and
changing a position of the stage relative to the incidence.

9. The system of claim 8, wherein the scan region has a second care area, the controller is further configured to instruct the optical inspection tool to optically scan:

a second portion of the scan region within the die at the fast feed rate, wherein the second portion of the scan region is not within the first care area nor within the second care area; and the second care area within the die at the slow feed rate.

10. The system of claim 8, wherein changing the position of the stage relative to the incidence comprises moving one or more of the stage, the light detector, the light emitter, or the light beam.

11. The system of claim 8, wherein the magnitude of the fast feed rate is two to four times the magnitude of the slow feed rate.

12. The system of claim 8, wherein the first care area comprises a polygonal boundary.

13. The system of claim 8, wherein the light detector is a time delay and integration image sensor.

14. The system of claim 8, wherein the first care area comprises a redistribution layer region and the first portion of the scan region is not the redistribution layer region.

15. A non-transitory computer-readable storage medium, comprising one or more programs for executing the following steps on one or more computing devices:
instruct an optical inspection tool to:
receive a scan region of a die having a first care area;
send instructions to the optical inspection tool to emit a light beam; and
send instructions to the optical inspection tool to change a position of a stage relative to an incidence of the light beam, thereby optically scanning:
a first portion of the scan region within the die at a fast feed rate, wherein the first portion of the scan region is not within the first care area; and
the first care area within the die at a slow feed rate.

16. The non-transitory computer-readable storage medium of claim 15, wherein the scan region has a second care area, and wherein instructing the inspection tool further includes optically scanning:
a second portion of the scan region within the die at the fast feed rate, wherein the second portion of the scan region is not within the first care area nor within the second care area; and the second care area within the die at the slow feed rate.

17. The non-transitory computer-readable storage medium of claim 15, wherein the magnitude of the fast feed rate is two or four times the magnitude of the slow feed rate.

18. The non-transitory computer-readable storage medium of claim 15, wherein the first care area comprises a polygonal boundary.

* * * * *